US008560271B2

(12) United States Patent
Koehler et al.

(10) Patent No.: US 8,560,271 B2
(45) Date of Patent: Oct. 15, 2013

(54) METHOD FOR MONITORING THE OPERATION OF A MEDICATION DELIVERY DEVICE, AN ELECTRONIC MODULE, AND A MEDICATION DELIVERY SYSTEM

(75) Inventors: Matthias Koehler, Laudenbach (DE); Peter Blasberg, Weinheim (DE); Christoph Cronrath, Lautersheim (DE); Frank Deck, Niederkirchen (DE); Hanspeter Heiniger, Lotzwil (CH); Manfred Aigner, Heimstetten (DE); Bernhard Guennewig, Geisenfeld (DE); Alfred Kloos, Unterhaching (DE); Genrikh Siris, Taufkirchen (DE)

(73) Assignees: Roche Diagnostics Operations, Inc., Indianapolis, IN (US); Roche Diagnostics International Ltd., Rotkreuz (CH)

( * ) Notice: Subject to any disclaimer, the term of this patent is extended or adjusted under 35 U.S.C. 154(b) by 980 days.

(21) Appl. No.: 12/606,644

(22) Filed: Oct. 27, 2009

(65) Prior Publication Data

US 2010/0145656 A1 Jun. 10, 2010

(30) Foreign Application Priority Data

Oct. 28, 2008 (EP) ..................................... 08018817

(51) Int. Cl.
*G06F 11/30* (2006.01)
(52) U.S. Cl.
USPC ......................................................... 702/182

(58) Field of Classification Search
USPC ......................................................... 702/182
See application file for complete search history.

(56) References Cited

U.S. PATENT DOCUMENTS 5,389,078 A * 2/1995 Zalesky et al. ................ 604/151

FOREIGN PATENT DOCUMENTS

| EP | 1095668 B1 | 4/2007 |
|---|---|---|
| EP | 1776975 A2 | 4/2007 |
| WO | 03/074110 A1 | 9/2003 |
| WO | 2005/025652 A1 | 3/2005 |
| WO | 2006/120253 A2 | 11/2006 |
| WO | 2007/053779 A2 | 5/2007 |
| WO | 2007/107564 A1 | 9/2007 |

* cited by examiner

*Primary Examiner* — Stephen Cherry
(74) *Attorney, Agent, or Firm* — Roche Diagnostics Operations, Inc.

(57) ABSTRACT

The disclosure relates to a method for monitoring the operation of a medication delivery device, the method comprising the steps of: providing a medication delivery device, the medication delivery device comprises a medication delivery module, providing an electronic module coupled to the medication delivery device, the electronic module comprises a sensor element, a control element, and a storing element, detecting, using the sensor element, signals generated in response to a measurable operation of the medication delivery module, generating electronic data by processing, using the control element, electronic information derived from the detected signals, the electronic data comprises information about a medication delivery characteristic of at least one measurable operation of the medication delivery module, and storing the electronic data in the storing element.

5 Claims, 5 Drawing Sheets

METHOD FOR MONITORING THE OPERATION OF A MEDICATION DELIVERY DEVICE, AN ELECTRONIC MODULE, AND A MEDICATION DELIVERY SYSTEM

REFERENCE

This application is based on and claims priority to European Patent Application No. EP 08 018 817.0 filed 28 Oct. 2008, which is hereby incorporated by reference.

FIELD

The disclosure relates to a method for monitoring the operation of a medication delivery device, an electronic module adapted to be coupled on an associated medication delivery device, and a medication delivery system.

BACKGROUND

Medication delivery devices are used in various embodiments, in order to prepare one or more medications to be dispensed. Such devices are also used in veterinary medicine. For example, such medication delivery devices are intended for use in the dispensing of insulin.

A medication delivery device is known from document WO 2007/107564 in a mechanical design. It comprises an embodiment as a pen. Through mechanical operation, an amount of liquid medication (bolus) from an ampoule provided is expelled, in order to be administered. In the case of the known device, an electronic module is provided which is configured to register events or actions which occur in the medication delivery device by detecting signals and to prepare electronic data for the signals measured and to give them a respective time stamp. The measurable signals can be acoustic signals or vibration signals. The electronic data produced are stored and can be read by means of a wireless interface. The signals detected are to be allocated, in particular, to a dispensation of a dose of the medication or an adjustment process, through which a dose has been regulated.

SUMMARY

Embodiments of the invention provide a method for monitoring the operation of a medication delivery device, an electronic module adapted to be coupled on an associated medication delivery device, and a medication delivery system, wherein a more reliable use of the medication delivery device is supported.

According in one embodiment of the invention, a method for monitoring the operation of a medication delivery device is provided, the method comprises the steps of: providing a medication delivery device, the medication delivery device comprising a medication delivery module, providing an electronic module coupled to the medication delivery device, the electronic module comprising a sensor element, a control element, and a storing element, detecting, using the sensor element, signals generated in response to a measurable operation of the medication delivery module, generating electronic data by processing, using the control element, electronic information derived from the detected signals, the electronic data comprising information about a medication delivery characteristic of at least one measurable operation of the medication delivery module, and storing the electronic data in the storing element.

According to another embodiment of the invention, an electronic module adapted to be coupled to an associated medication delivery device is provided, the electronic module comprises: coupling means configured to couple to an associated medication delivery device, a sensor element configured to detect signals generated in response to a measurable operation of the medication delivery module provided within the associated medication delivery device, a control element configured to generate electronic data by processing electronic information derived from the detected signals, the electronic data comprising information about a medication delivery characteristic of at least one measurable operation of the medication delivery module, and a storing element configured to store the electronic data.

According to still another embodiment of the invention, a medication delivery system is provided, the system comprises an electronic module which is coupled to an associated medication delivery device. The medication delivery system may also be referred to as a medication delivery assembly.

In certain embodiments, the electronic module as a whole or some of the elements provided in the electronic module are integrated into the medication delivery device. For example, this can be achieved by a non-releasable coupling of the electronic module or at least some of its elements to the medication delivery device. The electronic module may alternatively be implemented as a portable electronic module, which in one embodiment can be adapted for a releasable coupling on the medication delivery device.

The medication delivery device is provided with a mechanical mechanism for medication delivery. Such medication delivery device is sometimes referred to as a mechanical medication delivery device. It may also be referred to as an electronic medication delivery device which comprises, in addition, one or more electronic components, such as an electronic display and a power source providing electric energy for one or more electronic components.

Embodiments of the invention improve the use of a medication delivery device, such as a mechanical or electronic insulin delivery device, is made easier and more reliable for the patient. Embodiments of invention enable properties of the medication dispensing to be automatically detected upon use of the mechanical medication delivery device in order to make them available for analysis. In addition to registering event information about whether the event happened or not, embodiments of the invention characterize the medication dispensing event(s) using sensors. Information about the characteristics of the medication dispensing event, for example, may also be derived from an analysis of the characteristic of the signals measured. For example, the time course and/or the waveforms of the signals measured can be analyzed.

In one embodiment, the step of detecting the signals comprises a step of using at least one of a piezoelectric sensor, a pressure sensor, a vibration sensor, a touch contact sensor, a distance sensor, a flow sensor, and an optical sensor. The distance sensor may be provided as an inductive or capacitive sensor device. With the help of the piezoelectric sensor, the pressure sensor, the vibration sensor, the touch contact sensor or the distance sensor, in particular from events of operation of the medication delivery module can be detected which can be attributed to the dispensing of a bolus or a dose, i.e. the dispensing of an amount of the medication. One or more of the above sensor types can be integrated into the sensor element. The distance sensor can be used, in particular, to detect movements, preferably movement characteristics, of one or more components of the medication delivery device. These can be radial movements, e.g. the turning of the adjustment knob, which is turned upon operation of the medication delivery module. The detection of the movement of a component can alternatively or additionally be made through means of an optical sensor with which both a parallel translational or a rotational movement can be detected. The use of one or more types of sensor enables the detection of events, which arise as a measurable reaction to the operation of the medication delivery module. The processing of the information derived from these detected signals can, for example, allow conclusions to be drawn as to the amount of fluid dispensed by the medication delivery device, for example the amount of insulin. This can be deduced from the multiplication of the size of the bolus and the number of dispensing events if these are both known. Electronic data, which has been thus generated can then be stored. Signals can be detected through the use of a flow sensor, which may then be analysed in respect of flow amount and flow time. The flow sensor can be provided as an infrared, ultrasound, inductive or capacitive sensor. The various information about medication dispensing event(s) characteristics may be stored together with a time stamp.

According to a further embodiment, the step of generating electronic data comprises a step of generating information about a measurable priming operation of the medication delivery module. The operation of the medication delivery module prior to the actual injection is referred to as a priming operation. In particular, air is hereby expelled which is located in a cartridge or ampoule with the medication in order to prevent injection of air occurring when the patient uses the medication delivery module. For this purpose, the medication delivery device is usually brought into a position which causes the air to rise in order that it may be expelled by operating the medication delivery module. In this way, in one embodiment of the invention a positioning sensor may be provided in order to detect the spatial position of the medication delivery device, which may be evaluated as an indication of a priming operation. The delivery events detected with a particular spatial location of the medication delivery device shall be considered priming operations. An amount of the medication which may be hereby expelled can be taken into account, namely deducted, when information about an effectively delivered amount of the medication is calculated and stored.

In still a further embodiment, the step of generating electronic data comprises a step of generating information about an event of expelling air caused by the at least one measurable operation of the medication delivery module. The expelling of air occurs in particular in connection with the priming operation of the medication delivery module. The information about an expulsion of air can, for example, be derived from signals which are detected with the help of a force sensor, as such a sensor can be used to measure a flow resistance upon expulsion of a liquid, whereby the flow resistance in the case of an expulsion of air differs from the flow resistance in the case of an expulsion of a liquid. A pressure sensor can also be used in order to detect signals which may be analysed in respect of an event of expelling air. In one embodiment, the possibility can be provided to calculate, from the information about events of expelling air and the amount expelled, how much air has been discharged.

According to one embodiment, the step of generating electronic data comprises a step of generating information about an expelling characteristic of an expelling event caused by the at least one measurable operation of the medication delivery module. Expelling or discharging characteristics can affect various features of the expelling event. For example, resistance to the discharged fluid can be measured, and from this conclusions can be drawn as to whether healthy or scarred tissue has been penetrated. For this purpose, resistance values measured can be compared to pre-stored comparative values in order to draw conclusions from this. Information about resistance offered can be derived, for example, from the shape of the signal measured. Signal waveforms can occur whereby the signals plotted over time contain curves with one or both steep sides. In contrast to this, flatter upward or downward curves are created with different resistances. Information on the resistance can thus, amongst other things, be derived from the signal waveforms. Also, from the signal waveforms information about an injection velocity in the process of medication delivery may be gathered.

In another embodiment, the step of processing the electronic information derived from the detected signals comprises a step of analyzing a signal feature characteristic of the detected signals. The signal feature characteristics can, for example, relate to the shape of the signal waveform. An analysis of the integrated area of the signals can be provided for.

With respect to the electronic module adapted to be coupled on an associated medication delivery device, the following features are disclosed.

The coupling means may be configured for detachably or non-detachably coupling the electronic module on the associated medication delivery device.

In an embodiment, the sensor element comprises at least one of a piezoelectric sensor element, a pressure sensor, a vibration sensor, a touch contact sensor, a distance sensor, a flow sensor, and an optical rotation sensor.

According to a further embodiment, a plurality of connectable housing elements is provided. The connectable housing elements may be adapted to form the coupling means. It may be configured such that the coupling means can be formed with the help of the construction of the housing elements.

In still a further embodiment, the coupling means comprise a receptacle configured to receive a housing portion of the associated medication delivery device.

According to another embodiment, the receptacle is configured to at least partially encompass a housing of the associated medication delivery device.

In another embodiment, the receptacle is provided with an opening. This embodiment can be configured such that the electronic module is attached on top of the housing of the medication delivery device in that the housing is inserted into the opening.

In another embodiment, the coupling means are configured to couple to an end portion of the housing of the associated medication delivery device. An adjustment knob, for example, can be provided in the end portion of the housing which can be used to adjust the size of the bolus. In one embodiment, the electronic module can then be attached to the adjustment knob.

According to a further embodiment, the control element is further configured to generate, in the step of generating electronic data, information about a measurable priming operation of the medication delivery module.

In still a further embodiment, the control element is further configured to generate, in the step of generating electronic data, information about an event of expelling air caused by the at least one measurable operation of the medication delivery module.

According to an embodiment, the control element is further configured to generate, in the step of generating electronic data, information about an expelling characteristic of an expelling event caused by the at least one measurable operation of the medication delivery module.

In another embodiment, the control element is further configured to analyze, in the step of processing the electronic information derived from the detected signals, a signal feature characteristic of the detected signals.

BRIEF DESCRIPTION OF THE DRAWINGS

Aspect of the invention will be described in further detail, by way of example, with reference to different embodiments. In the figures.

DETAILED DESCRIPTION

Figure 1:
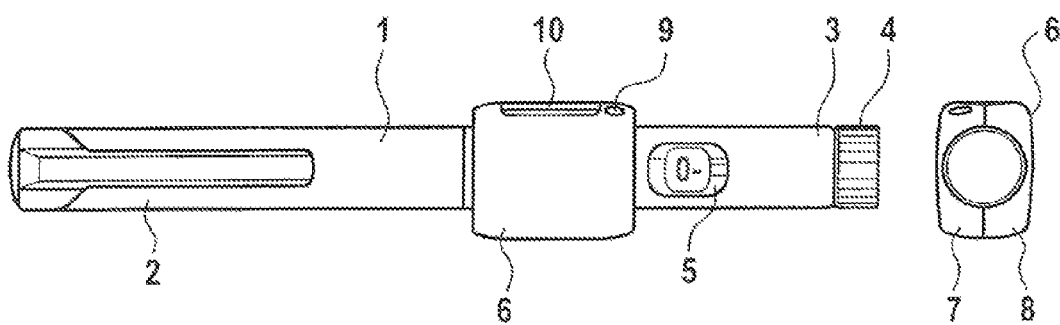
FIG. 1 shows a representation of a medication delivery device, namely a liquid delivery pen.

FIG. 1 shows a representation of a medication delivery device which is provided as a liquid delivery pen. In one embodiment, the liquid delivery pen is used to expel doses of insulin.

In a housing 1, a receptacle (not shown) is included, for example in the form of an ampoule or cartridge containing a medication to be dispensed. A detachable cap 2 is attached to the housing 1 so that the cap 2 may be removed in order to use the medication delivery device, whereupon a needle (not shown) is revealed through which doses of the medication to be dispensed may be dispensed. The dispensing of the dose (bolus) of medication occurs in that the patient presses the medication delivery device with the needle against the area into which the medication should be injected. This mechanical principle is known as such for various medication delivery devices.

In the area of an end portion 3, an adjustment knob 4 is attached, which may be turned in order to regulate the relevant dose of medication which should be dispensed when the medication delivery device is used. A value will be displayed in a display window 5 corresponding to the setting.

An electronic module 6 is coupled to the housing 1 of the medication delivery device which, as per the representation in FIG. 1 which shows the medication delivery device from the side and from the back, comprises two housing sections 7, 8 which, in the embodiment shown, are detachably or, in an alternative embodiment, non-detachably attached to each other and totally encompass the housing 1.

A sensor element is provided in the electronic module 6 to detect measurement signals, a control element is provided to process the detected measurement signals or electronic information derived from them as well as a storing element to store the electronic data. The electronic module 6 also has a power supply, for example in the form of one or more rechargeable batteries. Further, the electronic module 6 contains activation means 9. The activation means 9 provide the user with the option to activate or deactivate a data interface 10 which is configured to allow wireless data exchange. The deactivation of the data interface 10 can prevent unnecessary energy consumption. The data interface may be configured for different technologies such as radio frequency, Bluetooth, near field communication, or infrared data communication.

In addition, an interface is provided for the electronic module 6 through which data may be read from or inputted into the electronic module 6 by means of wireless or wired data communication in particular from or into the storing element. In a preferred embodiment, a connection element (not shown) is provided for the electronic module 6, for example a plug socket through which a connection to a power supply can be made in order to recharge the rechargeable batteries.

Figure 2:
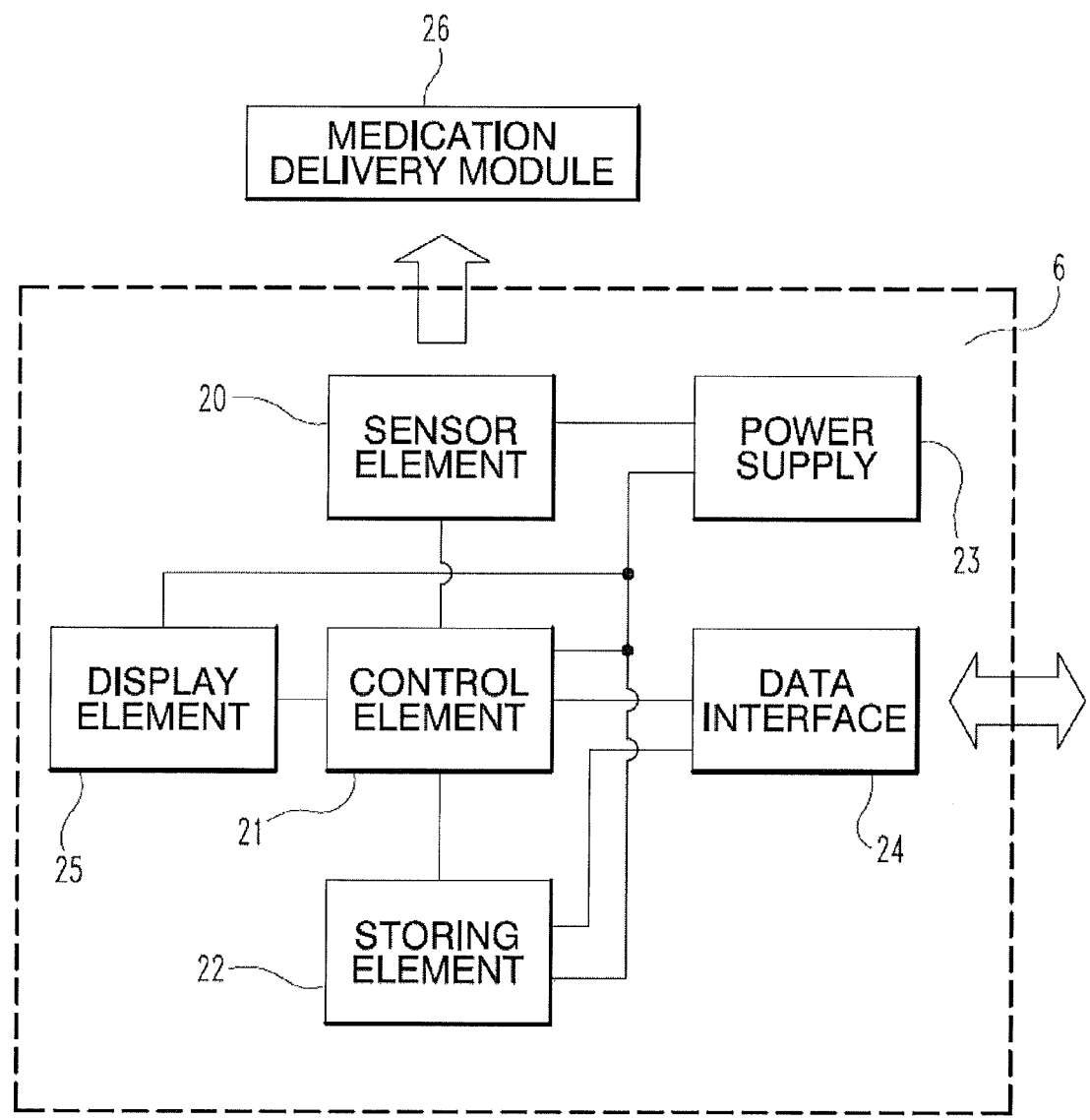
FIG. 2 shows a schematic representation of an electronic module.

FIG. 2 shows a schematic representation of an electronic module as it is used with the medication delivery device in FIG. 1.

The electronic module is provided with a sensor element 20, a control element 21, a storing element 22, a power supply 23, as well as a data interface 24. A display element 25 is also shown. Through the sensor element 20, an operation of a medication delivery module 26 is detected whereby this can occur directly at the medication delivery module 26 or indirectly by means of the detection of a detectable measurement amount caused by it. The sensor element 20 comprises one or more types of sensor from the following group of sensor types: piezoelectric sensor, pressure sensor, vibration sensor, touch contact sensor, distance sensor, flow sensor, optical sensor. The sensor element 20 with one or more sensors, serves to detect measurement signals, which arise as a reaction to the operation of a medication delivery module 26 in the medication delivery device as shown by way of example in FIG. 1. These signals reflect the operation of the medication delivery module 26 by the user.

The signals detected or electronic information derived from them are then further processed with the help of the control element 21 which in turn comprises, for example, a microprocessor, in order to obtain electronic data which contain information about the characteristics of the medication delivery of the detected operation of the medication delivery module 26. In order to obtain such electronic information, the data derived from the signals can be combined, compared and/or jointly processed with the data provided in the electronic module 6. The data provided in the electronic module 6 can comprise either pre-stored comparative data which was transferred onto the module via the data interface 24 or which was created in the electronic module 6 itself in the course of previous data processing.

For example, it can be determined with the help of the data processing in the control element 21, in what amounts a medication has been expelled through one operation of the medication delivery device, in that, for example, from the knowledge of the number of operations of the medication delivery module and the respective amounts, the total amount of fluid expelled is determined.

In certain embodiments, the detected signals can be further analysed, for example, in respect of the shape of the signal measured or the signal waveform in order to obtain information about the process of expelling the medication. For example, it can be determined, from such an analysis of the signals, whether the fluid expelled, which can also comprise air in addition to the liquid medication which has been unintentionally enclosed in the cartridge with the medication encounters a higher or lower resistance which can, in turn, be interpreted as an indication of the properties of the material into which the injection was made. In this way, for example, one can determine whether the injection was made into healthy or scarred tissue. Information thus derived from the signals and the processing thereof can be stored in the storing element 22 in order to make them available for subsequent evaluation by the patient themselves or attending doctor. It can also be configured such that the user may be given feedback from this or other information directly upon use of the medication delivery device, for example in the form of a display on the electronic module 6. In this way, the user can be notified, for example, of an incorrect use or incorrect operation.

An analysis of the waveform of the signal can be used in order to determine whether liquid medication or air has been expelled. This is particularly relevant in connection with a so-called priming use, which usually provides for an expulsion of air, which may be contained in the cartridge with the medication, prior to the actual dispensing of the medication.

The electronic module 6 can be attached, in its various embodiments, to the medication delivery device, clipped on, stuck on, whereby the connection can be detachable or non-detachable.

Figure 3A:
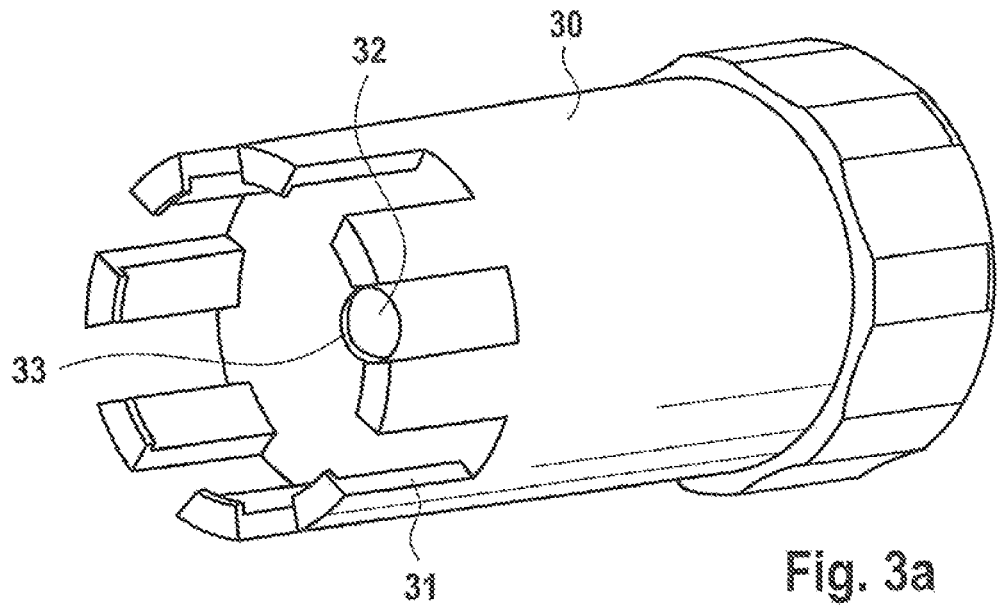
FIGS. 3a to 3c show schematic representations of a portable electronic module adapted to be coupled on an end portion of the medication delivery device in FIG. 1; and, FIGS. 4a to 4d show schematic representations of another portable electronic module adapted to be coupled on an end portion of the medication delivery device in FIG. 1.
Figure 3B:
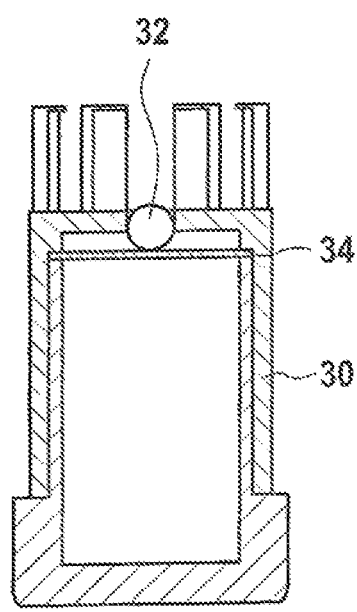
Figure 3C:
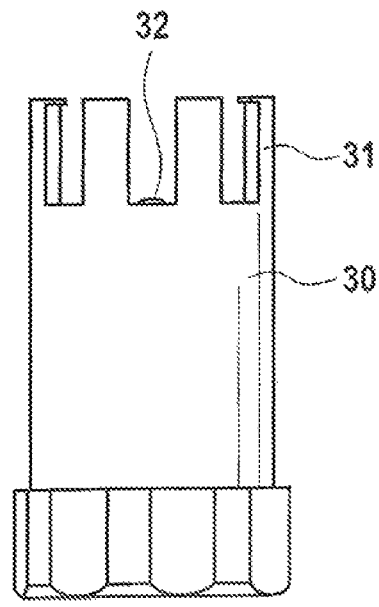
Figure 4A:
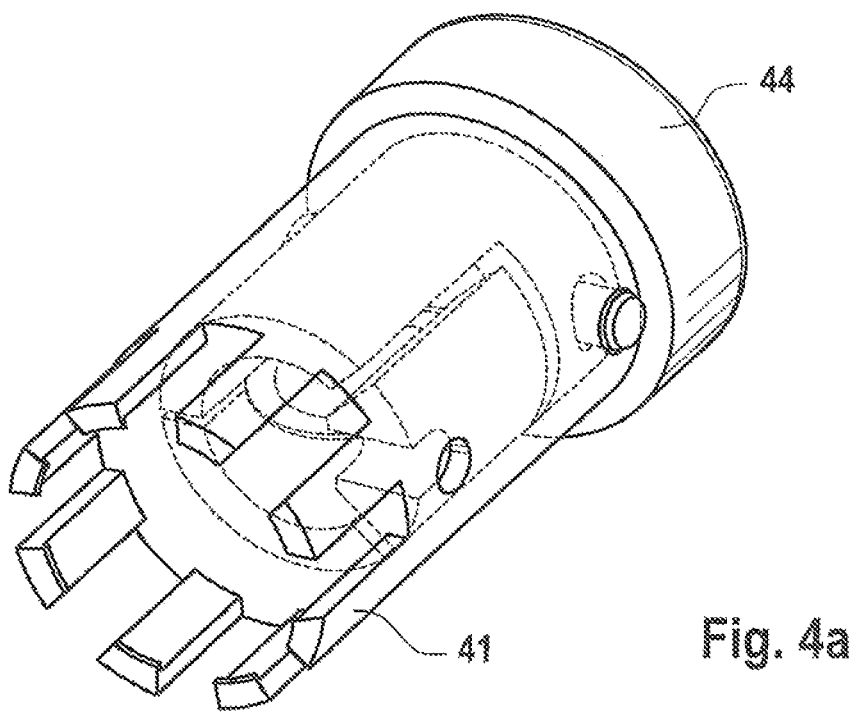
Figure 4B:
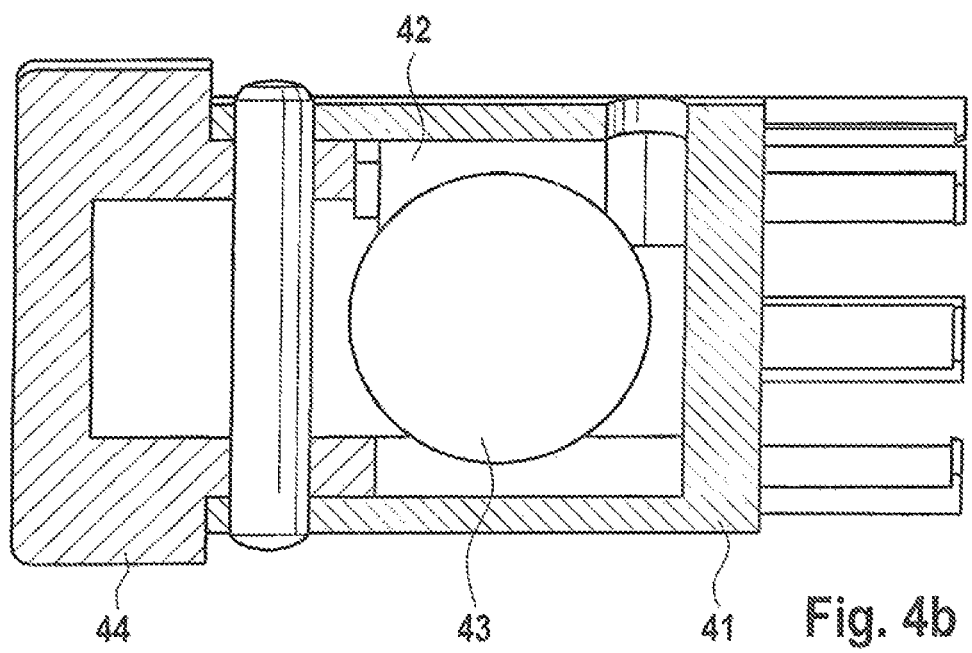
Figure 4C:
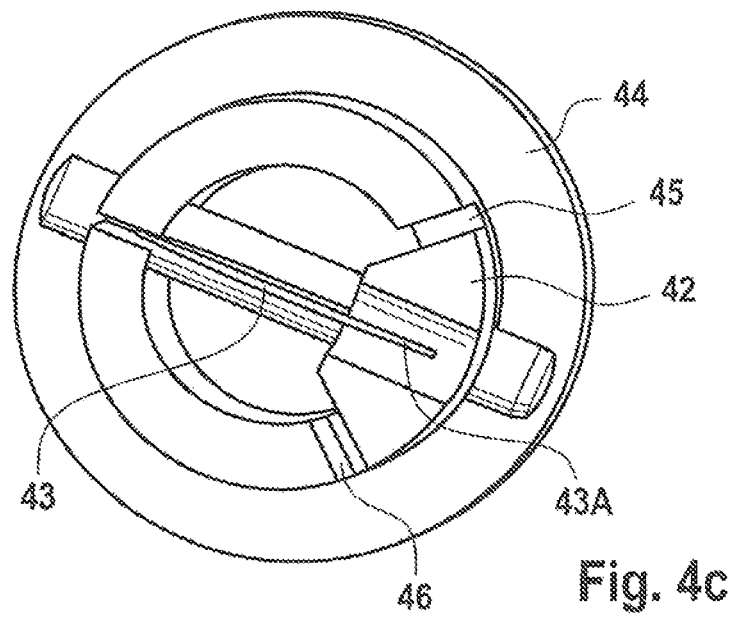
Figure 4D:
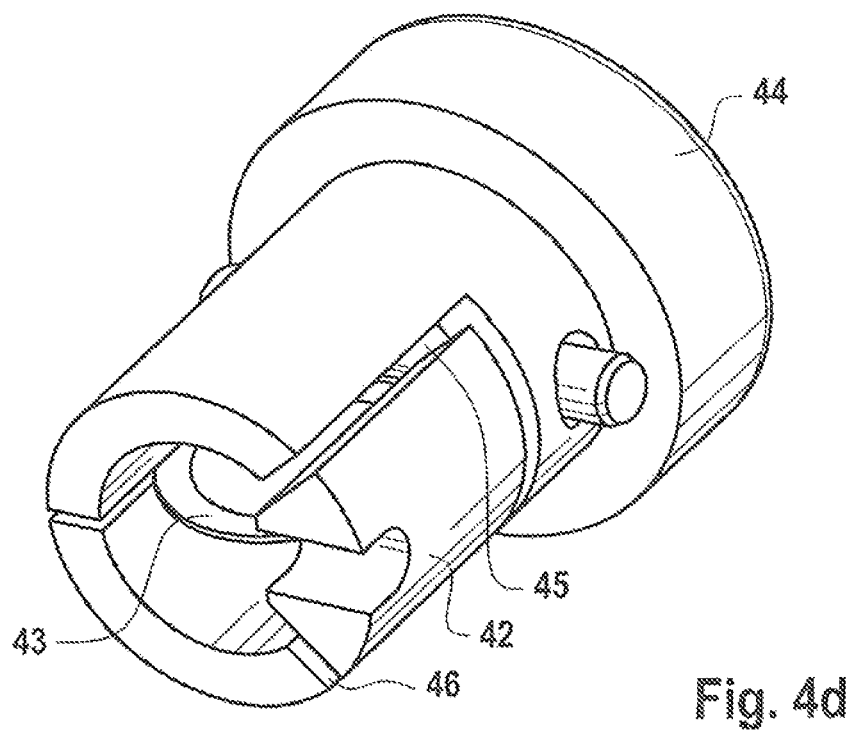

FIGS. 3a to 3c show schematic representations of a portable electronic module 30 adapted to be coupled on an end portion of the medication delivery device in FIG. 1.

Coupling means 31 are provided which are configured to couple the portable electronic module 30 to an end portion of the medication delivery device in FIG. 1, in particular the adjustment knob 4. This creates a coupling of a displaceable touch contact element 32, which is located in an opening 33 and coupled to a piezoelectric sensor 34, which is provided with a crystal disc. In the shown embodiment, the displaceable touch contact element 32 is provided with the shape of a sphere made of, for example, metal or plastic. The sphere shaping provides for safely detecting axial vibration, while effects due to other vibrations may be limited. Upon operation of the medication delivery module in the medication delivery device as per FIG. 1, there is pressure on the touch contact element 32 whereupon the events of operation in its characteristic are registered. The signals detected in this way can then be processed in the portable electronic module 30 as described above in reference to FIGS. 1 and 2. The descriptions in respect of the possible configuration and use of the electronic module 6 apply respectively to the portable embodiment in FIGS. 3a to 3c.

When contact pressure is provided to the piezoelectric sensor 34 an electric current will be generated in the piezoelectric sensor 34. In one embodiment, electric energy derived from such electric current is stored in electric energy storage means (not shown) which are located within the portable electronic module 30 and, for example, may be implemented with an electrical capacitor. The electric energy may be used for operation of electronic components of the portable electronic module 30 in the process of collecting data about the medication delivery, such as signal detection, and data storage. Such electrical energy management may even allow omitting a further energy sources.

FIGS. 4a to 4d show schematic representations of another portable electronic module 40 adapted to be coupled on an end portion of the medication delivery device in FIG. 1.

Coupling means 41 are provided which are configured to couple the portable electronic module 40 to an end portion of the medication delivery device in FIG. 1, in particular the adjustment knob 4. The coupling means are provided as a clamp device. The coupling means 41 are fixed on a receiver 42. The receiver 42 supports a piezoelectric sensor 43 provided with a crystal disk 43A. End portions of the piezoelectric sensor 43 are located in two openings provided in the receiver 42. The piezoelectric sensor 43 is in contact with adjustment means 44 provided with a rotary knob. Air gaps 45, 46 provide in the receiver 42 allow for a rotation of the adjustment means 44 relative to the receiver 42.

Upon operation of the medication delivery module in the medication delivery device as per FIG. 1, there is pressure on the piezoelectric sensor 43 whereupon the events of operation are registered. The signals detected in this way can then be processed in the portable electronic module 40 as described above in reference to FIGS. 1 and 2. The descriptions in respect of the possible configuration and use of the electronic modules 6 and 30, respectively, apply respectively to the portable embodiment in FIGS. 4a to 4d.

Thus, embodiments of the method for monitoring the operation of a medication delivery device, an electronic module, and a medication delivery system are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A liquid delivery pen for delivering medication, comprising:
   a medical delivery module, comprising
      a housing in the shape of a pen having an end portion and a receptacle configured to carry an internal cartridge containing medication;
      a detachable cap coupled to the housing opposite the end portion covering a needle and when the detachable cap is removed a needle is revealed;
      an adjustment knob coupled to the housing end portion rotatable to regulate the dose of medication to be dispensed having a display window to show the value of medication to be dispensed; and
   an electronic module coupled to the housing, comprising,
      a power supply for powering components of the electronic module
      a sensor element to detect measurement signals from axial vibration arising from operation of the medical delivery module,
      a control element to process measurement signals from the sensor element into electronic data,
      a storing element to store electronic data generated by the control element,
      a data interface coupled to the storing element to provide wireless data exchange using one of radio frequency communications, near field communications, or infrared communications, and
      activation means to activate or deactivate the data interface to provide data interchange.

2. The liquid delivery pen of claim 1 wherein, the electronic module is configured as a means for coupling attached to the end portion of the housing, the means for coupling carrying a touch contact element that is coupled to a piezoelectric sensor to detect axial vibration and generate measurement signals that are processed by the control element and stored by the storing element.

3. The liquid delivery pen of claim 2 wherein the touch contact element is a in the shape of a sphere.

4. The liquid delivery pen of claim 2 wherein the means for coupling also serves as the adjustment knob of the liquid delivery pen.

5. The liquid delivery pen of claim 2 wherein piezoelectric sensor detection of axial vibration is indicative of an expelling event.

* * * * *